United States Patent [19]

Foster

[11] Patent Number: 5,699,909
[45] Date of Patent: Dec. 23, 1997

[54] SURGICAL INSTRUMENT PACKAGE

[75] Inventor: Brian W. Foster, Trumbull, Conn.

[73] Assignee: United States Surgical Corporation, Norwalk, Conn.

[21] Appl. No.: 693,746

[22] Filed: Aug. 7, 1996

[51] Int. Cl.⁶ .................................................. B65D 85/20
[52] U.S. Cl. ........................... 206/370; 206/438; 206/485; 206/486
[58] Field of Search ........................ 206/363, 364–370, 206/438, 439, 485, 486, 476; 383/103

[56] References Cited

U.S. PATENT DOCUMENTS

| | | |
|---|---|---|
| 1,367,600 | 2/1921 | Hirsch . |
| 2,024,984 | 12/1935 | Bradley . |
| 2,947,415 | 8/1960 | Garth . |
| 3,013,656 | 12/1961 | Murphy, Jr. . |
| 3,405,860 | 10/1968 | Manizza .................. 206/485 |
| 3,411,620 | 11/1968 | Steinbock . |
| 3,768,725 | 10/1973 | Pilaro ...................... 206/439 |
| 3,802,555 | 4/1974 | Grasty et al. . |
| 3,937,219 | 2/1976 | Karakashian ............. 206/439 |
| 4,023,678 | 5/1977 | Fiedler . |
| 4,332,322 | 6/1982 | Jaeschke et al. . |
| 4,420,077 | 12/1983 | Reccaforte .............. 206/485 |
| 4,511,035 | 4/1985 | Alpern . |
| 4,573,576 | 3/1986 | Krol . |
| 4,630,729 | 12/1986 | Hirt et al. . |
| 4,660,721 | 4/1987 | Mykleby .................. 206/438 |
| 4,714,595 | 12/1987 | Anthony et al. .......... 383/103 |
| 4,811,847 | 3/1989 | Reif et al. . |
| 4,954,239 | 9/1990 | Mueller . |
| 5,076,431 | 12/1991 | Thompson . |
| 5,082,112 | 1/1992 | Dunklee . |
| 5,131,542 | 7/1992 | Stenström . |
| 5,199,561 | 4/1993 | Roshdy et al. . |
| 5,226,535 | 7/1993 | Rosdhy et al. . |
| 5,234,106 | 8/1993 | Transue et al. . |
| 5,284,244 | 2/1994 | O'Toole et al. . |
| 5,315,985 | 5/1994 | Decarie et al. . |
| 5,323,905 | 6/1994 | Gerondale et al. . |
| 5,353,929 | 10/1994 | Foster . |
| 5,358,116 | 10/1994 | Brintazzoli ............... 206/485 |
| 5,375,717 | 12/1994 | Roshdy . |
| 5,413,217 | 5/1995 | Sauer . |
| 5,415,180 | 5/1995 | Horan . |
| 5,437,643 | 8/1995 | Transue . |
| 5,447,230 | 9/1995 | Gerondale . |
| 5,501,341 | 3/1996 | Van Es .................... 206/364 |

Primary Examiner—Paul T. Sewell
Assistant Examiner—Luan K. Bui

[57] ABSTRACT

A package for endoscopic surgical instruments includes a retainer member fabricated from a single sheet of flexible material. The retainer includes an arcuate portion forming a ridge extending laterally across the retainer. Apertures in the sloped sides of the arcuate portion are aligned for reception of the endoscopic portion of the surgical instrument, thereby securely holding the instrument. Distal and proximal upper flap portions fold over and interlock with each other to form the top of the retainer.

10 Claims, 7 Drawing Sheets

SURGICAL INSTRUMENT PACKAGE

BACKGROUND

1. Field of the Disclosure

The item described herein relates to packaging for instrumentation, and more particularly for surgical instrumentation such as that used in minimally invasive surgery.

2. Description of the Related Art

Various types of instrument packages are known for packaging elongated or endoscopic surgical instruments. One example of such packaging is shown in U.S. Pat. No. 5,144,942 issued to Decarie et al., which discloses a surgical kit packaged in a vacuum-formed, relatively rigid plastic enclosure having raised walls which correspond in size and shape to the instruments packages therein for retaining and displaying the instruments.

While such relatively rigid packaging has been commercially successful, there is a continuous need to provide easy to fabricate packaging at a low cost of manufacture. The packaging should also be easy to assemble and provide adequate protection to prevent damage to the instrument during shipping. The package described herein satisfies these needs.

SUMMARY

A package for an endoscopic surgical instrument is provided herein. The package includes an outer envelope and a retainer member disposed within the outer envelope. The retainer member is preferably a single integral sheet of flexible material extending lengthwise between a proximal end and a distal end. The sheet has first and second upper flap portions and a base, the first and second upper flap portions being joined to the base at fold regions respectively defining the proximal and distal ends of the retainer member when closed. The base has an arcuate portion forming a laterally extending ridge with proximal and distal sloping sides, each side having at least one aperture for reception therethrough of the endoscopic portion of a surgical instrument.

BRIEF DESCRIPTION OF THE DRAWINGS

Various embodiments are described herein with reference to the drawings wherein.

DETAILED DESCRIPTION OF PREFERRED EMBODIMENTS

Figure 1:
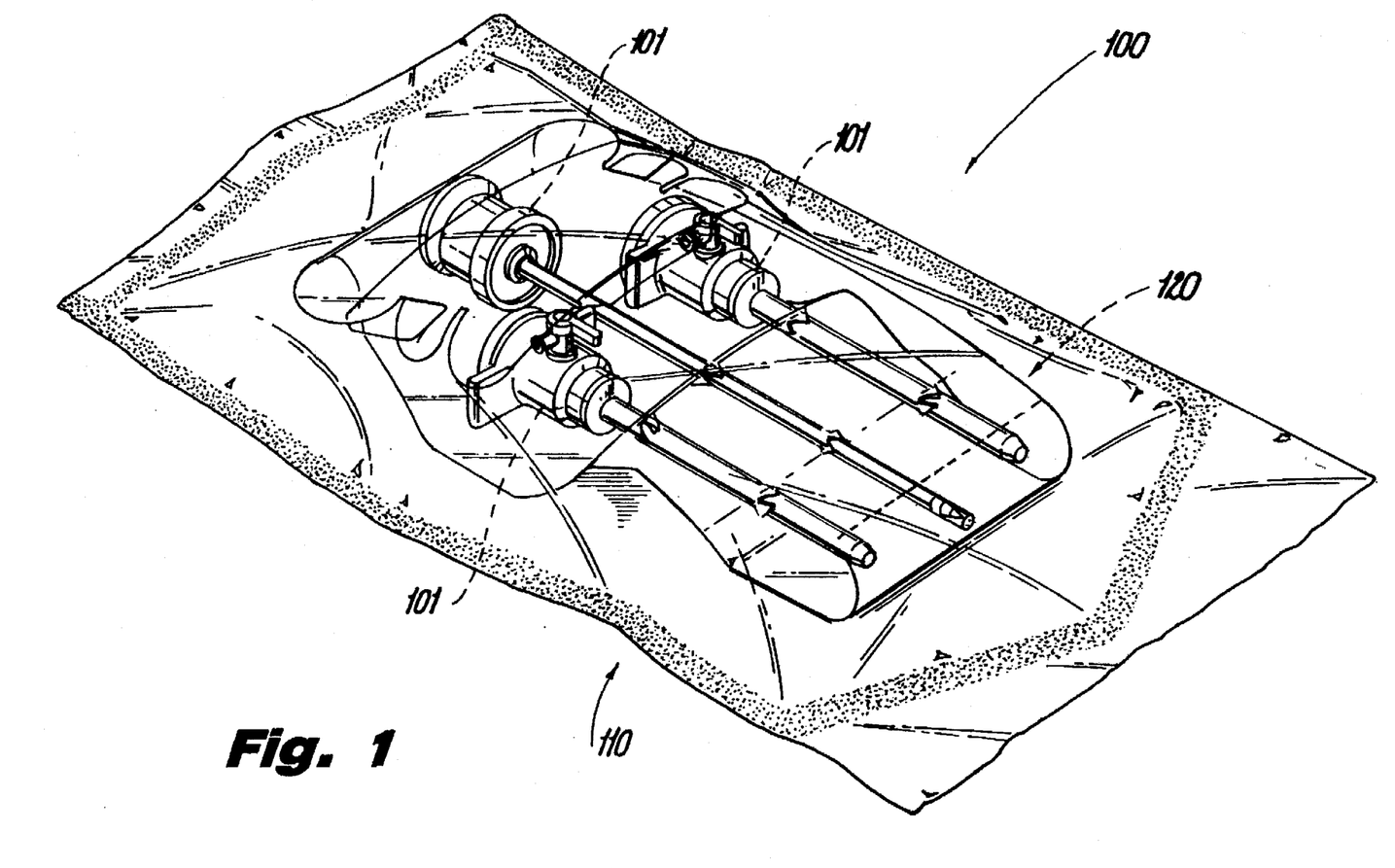
FIG. 1 is a perspective view of the surgical instrument package with instruments contained therein.

FIG. 1 illustrates a packaged surgical instrumentation kit 100 having at least one and preferably two or more surgical instruments 101, an outer envelope 110, and a retainer 120 for retaining the instruments 101.

Figure 2:
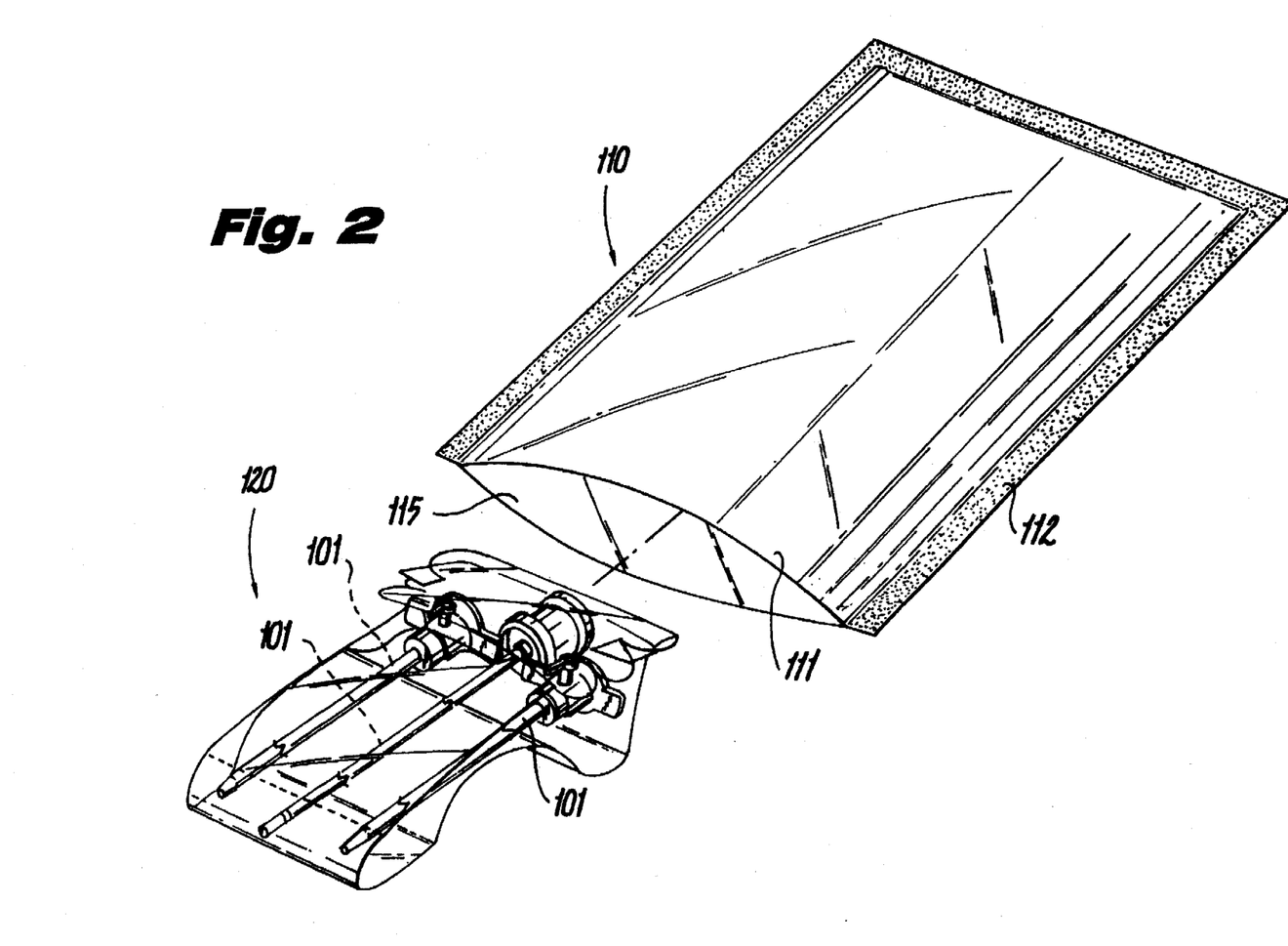
FIG. 2 is a perspective view of the retainer and instruments removed from the outer envelope.

Outer envelope 110 encloses the retainer 120 and surgical instruments 101. The outer envelope 110 is preferably a material impervious to fluids and capable of maintaining a sterile interior. For example, the outer envelope 110 can be fabricated from metal foil, or plastic sheet such as polyester, polypropylene copolymer, polyolefin, paper polyfoil, and combinations thereof. A preferred construction is illustrated in FIG. 2 wherein upper layer 111 is a clear plastic cover bonded around periphery 112 to a lower layer 115 of TYVEK® brand sheet of spunbonded polyolefin fiber. Bonding is achieved by any of the methods conventionally used in the art, such as heating, adhesives, and the like. The interior of the package can be sterilized by conventional means such as ethylene oxide, gamma irradiation, and the like.

The instruments 101 can be any type of instrument having an elongated narrow portion. However, the packaging described herein is especially advantageous for retaining and enclosing elongated surgical instruments such as those used in minimally invasive surgical procedures (e.g., laparoscopic or endoscopic surgery).

Figure 3:
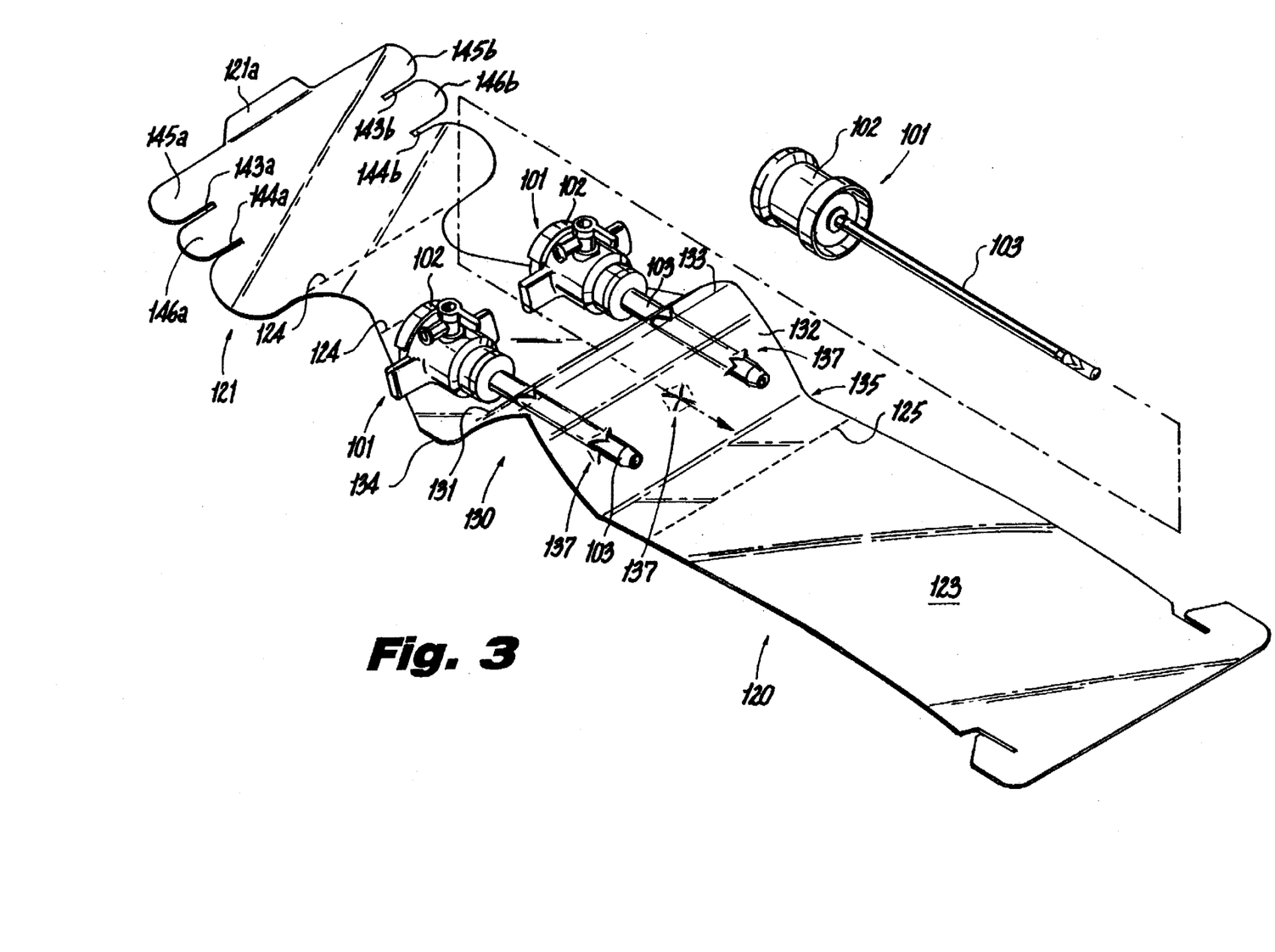
FIG. 3 is a perspective view of the retainer in an unfolded configuration showing instrumentation retained thereon.

As shown in FIG. 3, each instrument 101 includes a non-endoscopic portion 102 that remains outside the patient's body during the surgical procedure, and a long, narrow endoscopic portion 103 that is adapted to fit through a narrow cannula or a small incision or opening in the patient's body.

Figure 4:
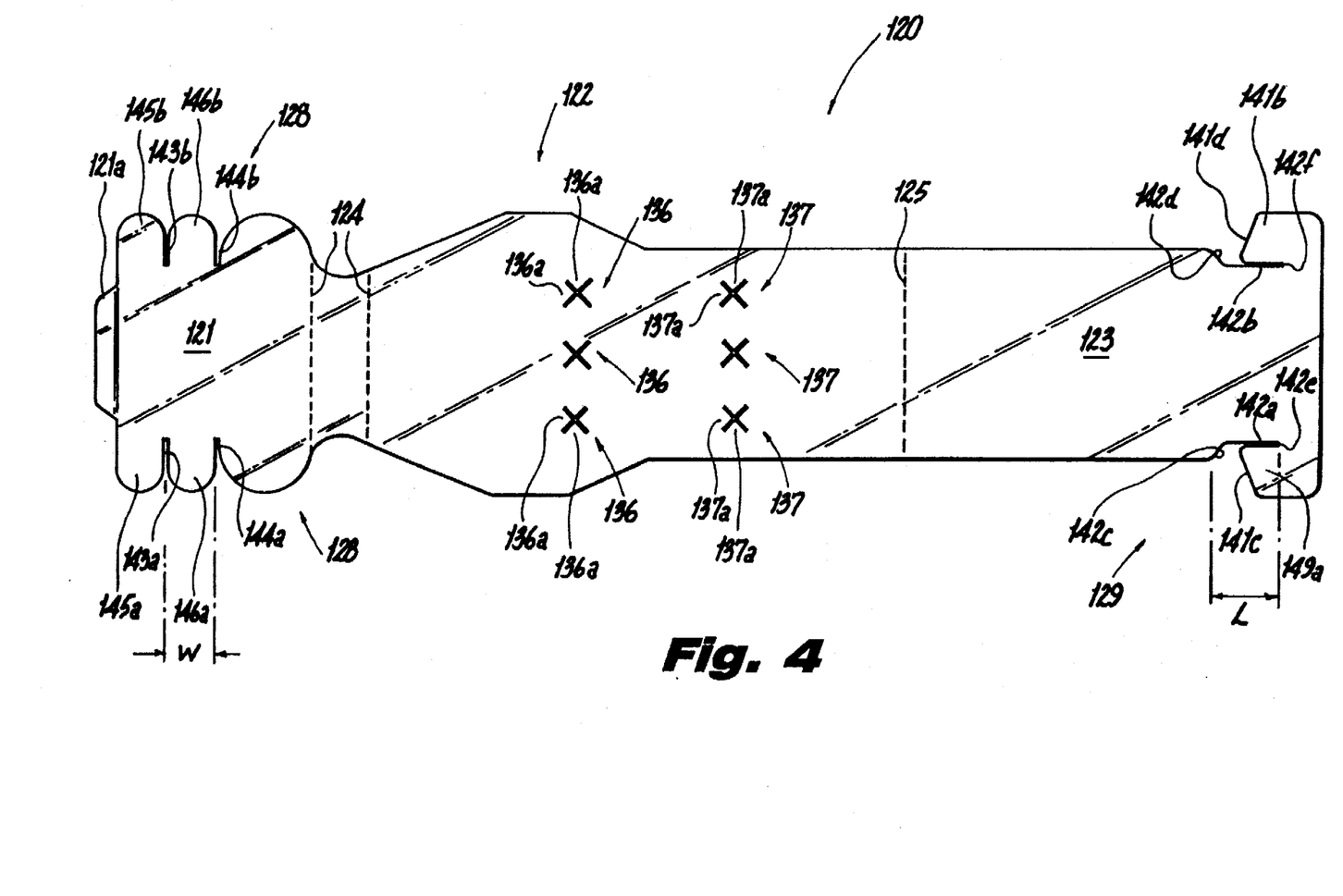
FIG. 4 is a plan view of the retainer strip in an unfolded configuration.

Referring also now to FIG. 4, the retainer 120 is fabricated from a single sheet of preferably transparent polymeric material such as polyethylene terephthalate, polyethylene, vinyl, polypropylene or ethylene vinyl acetate. Preferably, the retainer 120 is fabricated from olefinic hydrocarbon polymers such as polyethylene and/or polypropylene. The retainer 120 is flexible but retains sufficient resiliency to provide a cushioning effect against potentially damage during shipping and handling. Nevertheless, the retainer 120 is not as stiff as, for example, the vacuum formed polyethylene terephthalate holding member described in U.S. Pat. No. 5,144,942.

Figures 6, 7, 8:
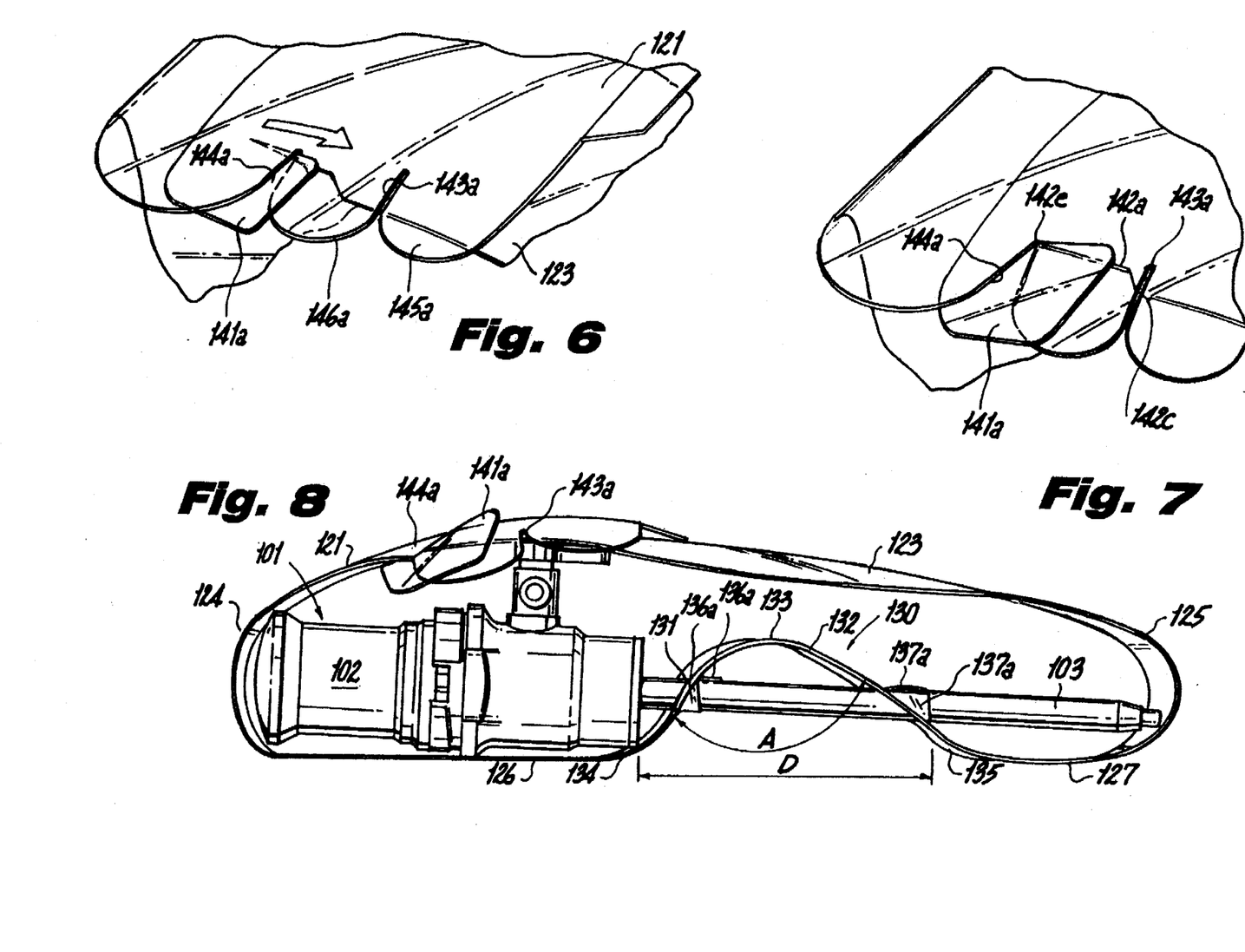
FIGS. 6 and 7 are cut-away perspective views showing engagement of the locking tabs and slots.
FIG. 8 is a side elevational view showing the instrument enclosed by the retainer.
Figure 9:
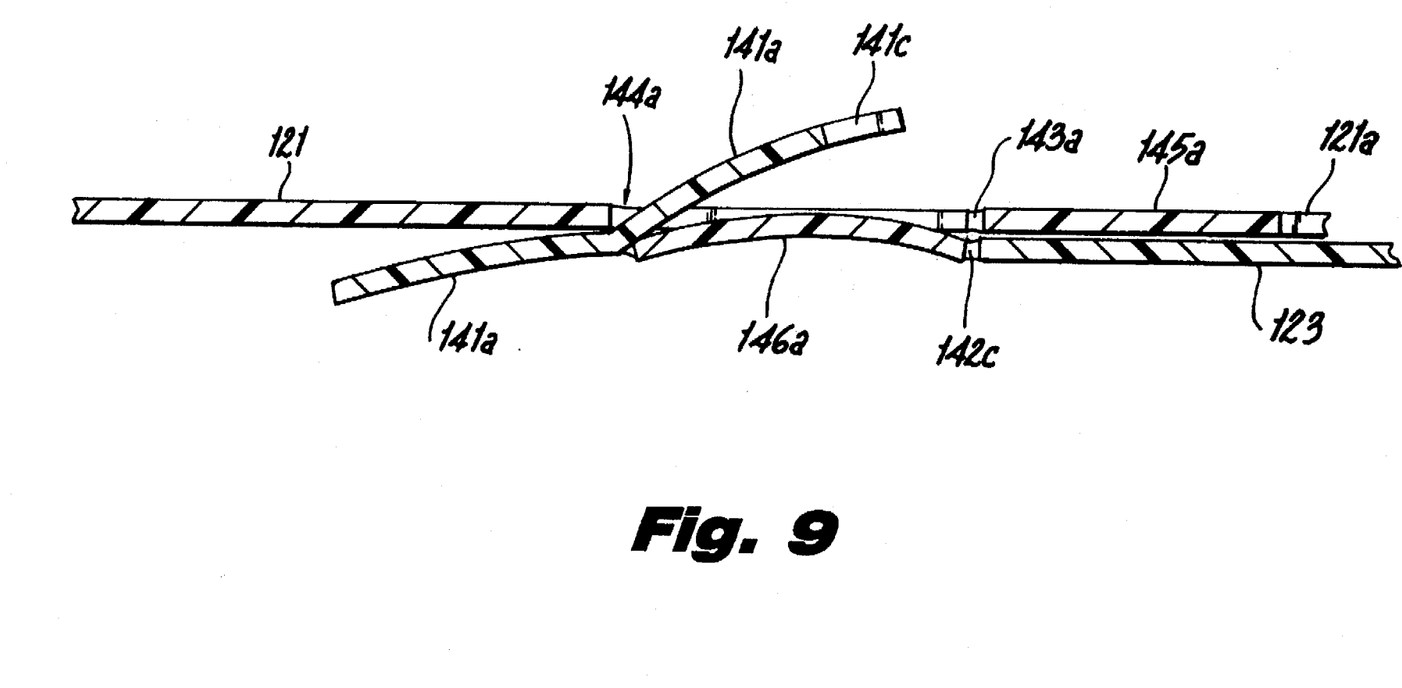
FIG. 9 is a sectional view of the engagement of the locking tab and slot.

Referring to FIGS. 3, 4 and 8 the retainer 120 includes a proximal flap 121, bottom portion 122 and distal flap 123, the terms "proximal" and "distal" being used relative to each other and referring to the retainer in a closed configuration. The terms "lengthwise" or "longitudinal" refer to the proximal-distal orientation. The term "lateral" refers to an orientation transverse to the longitudinal direction.

The bottom portion 122 includes a raised arcuate section forming an elongated ridge 130 with an apex 133 extending laterally across the insert 120. The ridge 130 is defined by proximal side 131 and distal sloped side 132 joined at the elongated apex 133. Ridge 130 is characterized by an angle A ranging from about 90° to about 170°, and more preferably from about 110° to about 140°. The sloped sides 131 and 132 intersect with unraised portions 126 and 127 of the bottom portion 122, respectively, at bend portions 134 and 135 respectively. The lengthwise distance D between bend portions 134 and 135 can be any distance suitable for the purposes described herein, but typically ranges from about 2" to about 6".

Referring to FIGS. 3, and 4 the proximal sloped side 131 includes at least one and preferably two or more apertures 136. The distal sloped side 132 includes at least one and preferably two or more apertures 137.

Proximal slope apertures 136 and distal slope apertures 137 are disposed laterally across the retainer 120. Each proximal slope aperture 136 is aligned with a corresponding distal slope aperture 137 in a lengthwise direction with respect to the retainer. The proximal slope aperture 136 and corresponding distal slope aperture 137 are adapted to receive the endoscopic portion 103 of the surgical instrument and hold it in longitudinal orientation with respect to the retainer. These apertures 136, 137 are preferably formed from X-shaped slits that define triangular flaps 136a and 137a, respectively, for resiliently holding the endoscopic portion 103 of the apparatus disposed therethrough. Optionally the retainer 120 can lay flat when initially made and in an unfolded configuration, as shown in FIG. 4, the ridge 130 being formed when endoscopic instruments are inserted through apertures 136 and 137, thereby causing the bottom portion 122 to bulge, forming ridge 130.

The distal flap 123 folds over the instrument and bottom portion 122 in a smooth bend without any significant bend line or crease. A distal score line 125 facilitates the bending of the distal flap 123.

The proximal flap 121 also folds over instrument 101 and the bottom portion 122 in a smooth creaseless bend, and also has at least one and preferably two proximal score lines 124 to facilitate the smooth curvature of the bend.

The proximal flap 121 and distal flap 123 have locking means 140 by which they can be engaged with each other to form a continuous cover over the instrument 101.

Referring now to FIGS. 3–6 and 8, the locking means 140 includes interlocking end portions: proximal interlocking end portion 128 of the proximal flap 121 and distal interlocking end portion 129 of the distal flap 123. Distal interlocking end portion 129 includes distally pointing (when the end portion is folded over) tabs 141a and 141b at least partially defined by slits 142a and 142b, respectively. Each slit 142a/142b terminates in a proximal end 142e and 142f, respectively, for abutment with proximal edges of lateral tabs 145a/145b and 146a/146b to prevent disengagement of the proximal and distal flaps 121 and 123, as explained below. The slits 142/142b terminate at their other end at flared portions 142c and 142d, respectively. The length of the slits L is the distance between these termination points. (See FIG. 4) Tabs 141a and 141b each have a distal edge 141c and 141d, respectively, which is angled with respect to the longitudinal axis of the retainer. This angular configuration facilitates the insertion of the tabs 141a and 141b into respective reception slots 143a/143b and 144a/144b on the proximal flap 121.

Proximal interlocking end portion 128 includes lateral slots 143a, 143b, 144a and 144b located near the edge of the proximal flap 121. The lateral slots are arranged in pairs such that slots 143a and 143b are linearly aligned with each other, slot 143a being positioned near one edge of the distal flap 123 and slot 143b being near the other edge. Slots 144a and 144b are positioned in a similar manner and are longitudinally spaced apart respectively from slots 143a and 143b. Slots 143a/143b and 144a/144b, at least partially define laterally extending tabs 145a/146b and 146a/146b. These lateral tabs have a rounded semicircular outer edge, and a width W which is approximately the same as length L of slits 142a and 142b.

Figure 5:
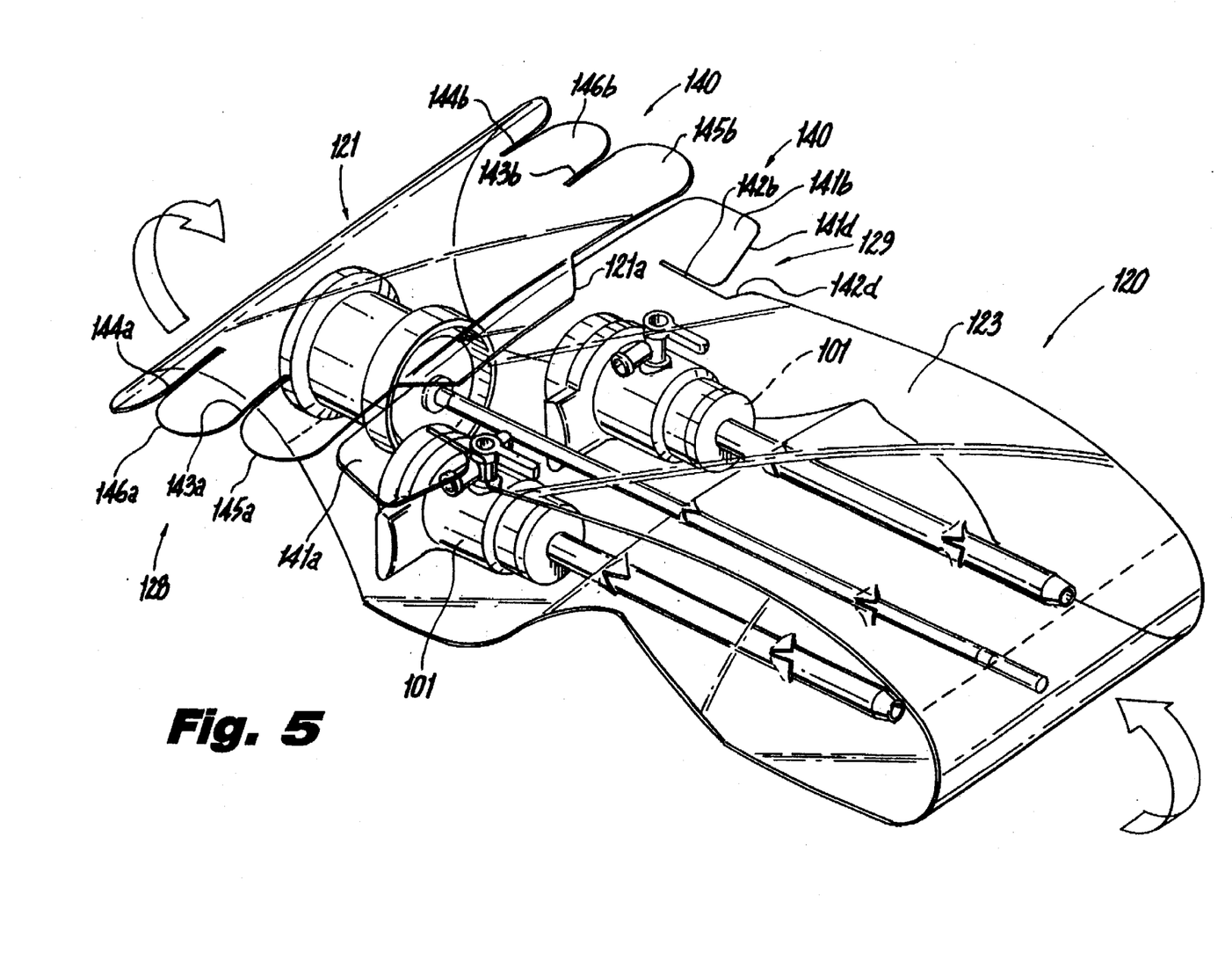
FIG. 5 is a perspective view showing the folding of the retainer to enclose the instruments.

Referring also now to FIGS. 6 and 7, slots 143a, 143b, 144a and 144b are adapted to receive tabs 141a and 141b, tab 141a being insertable into either slot 143a or 144a, and tab 141b being insertable into either 143b or 144b. When the tabs 141a/141b are engaged with slots 143a/143b or 144a/144b the proximal end portion 128 and distal end portion 129 are interlocked. Jostling and vibrations during shipping will not easily disengaged the locking means 140 (FIG. 5). However, intentional unlocking of the insert 120 is easily achieved by pulling the proximal flap 121 distally to disengage the tabs 141a/141b from the slots 143a/143b or 144a/144b. A pull tab 121a facilitates grasping of proximal flap 121.

It can be readily appreciated by one skilled in the art that the locking means 140 will resist disengagement of the interlocking end portions 128, and 129 by forces tending to move the proximal flap 121 proximally and the distal flap 123 distally. Such forces would only cause abutment of lateral tabs 145a/145b and 146a/146b against the proximal ends 142e and 142f of the slots 142a and 142b. Disengagement would be achieved only by mechanical failure of the plastic material from which the retainer 120 is constructed. However locking means 140 also includes means to resist opening in the normal manner, i.e. distal movement of the proximal flap 121, as mentioned above. This is achieved by flared edges 142c and 142d. Referring now to FIGS. 4, 6, 7, and 9, flared edges 142c and 142d provide an inclined abutment surface which contacts the distal edge of lateral tabs 145a/145b, 146a/146b when the locking means 140 is engaged. As can be seen from FIG. 9, engagement, for example, tab 141a in slot 144a tends to bias lateral-tab 146a downward. The length L of the slit 142a is substantially equal to width W of the lateral tab 146a. Thus, flared edge 142c tends to engage the distal edge of tab 146a when the proximal flap 121 is moved distally. The resistance to distal movement of the proximal flap 121 is predetermined by the angle of the flared edge 142c with respect to the longitudinal axis of the retainer. This resistance is overcome by the intentional opening of the retainer by a surgeon or other operating room personnel who can use a distally directed pulling and lifting motion on the proximal flap 121 to open the retainer 120. However, the forces caused by jostling tend to push downward on the proximal flap 121. The flared edge 142c therefore tends to offer selectively greater resistance to unintended opening of the retainer than to intended opening. This selectivity is also enhanced by the cooperative functioning between the outer envelope 110 and the flared edges 142c/142d in the following manner. when the retainer 120 is enclosed within the outer envelope 110 the proximal flap 121 is inhibited from being lifted. Hence, the flared edges 142c/142d tend to remain in engagement with the lateral tabs and unintended opening caused by jostling is avoided. After the retainer 120 is removed from the outer envelope 110 in the operating room, the proximal flap 121 is easily lifted and pulled.

It will be understood that various modifications may be made to the embodiments disclosed herein. Therefore, the above description should not be construed as limiting but merely as exemplifications of preferred embodiments. Those skilled in the art will envision other modifications within the scope and spirit of the claims appended hereto.

What is claimed is:

1. A package for a surgical instrument having an elongated endoscopic portion, which compromises:
   a) an outer envelope;
   b) a retainer member disposed within the outer envelope, the retainer member being a single integral sheet of flexible material extending lengthwise between a proximal end and a distal end, the sheet having a first upper flap portion, a second upper flap portion, and a base, the first upper flap portion being joined to the base at a proximal fold region defining the proximal end of retainer member, the second upper flap portion being joined to the base at a distal fold region defining the distal end of the retainer member, the base having an arcuate portion forming a ridge with a sloping proximal side and a sloping distal side, each of said sloping proximal and distal sides having at least one aperture for reception therethrough of an elongated portion of a surgical instrument, and c) locking means for engaging the first upper flap portion and the second upper flap portion.

2. The package of claim 1, wherein the outer envelope comprises first and second sheets of microorganism-impervious material bonded to each other around the periphery of each sheet.

3. The package of claim 2, wherein the second sheet is permeable to gas.

4. The package of claim 2, wherein the second sheet is fabricated from spun-bonded polyolefin fibers, and the first sheet is fabricated from a material selected from the group consisting of polymeric film and metal foil.

5. The package of claim 1, wherein the retainer member comprises a strip of flexible material selected from the group consisting of polyethylene terephthalate, polyethylene, vinyl, polypropylene and ethylene vinyl acetate.

6. The package of claim 1, wherein the apertures in the sloping distal and proximal sides of the ridge are aligned in a direction oriented with the lengthwise direction of the sheet of flexible material.

7. The package of claim 1, wherein at least one of the apertures is formed from an x-shaped slit.

8. The package of claim 1, wherein the ridge extends laterally across the retainer member.

9. The package of claim 1, wherein the locking means comprises at least one pair of linearly aligned slots in one of said first and second upper flap portions, and a pair of tabs on the other of said first and second upper flap portions for engaging said pair of linearly aligned slots.

10. The package of claim 9, further comprising a flared edge on one of said first and second upper flap portions to offer resistance to disengagement of the first and second flap portions.

* * * * *